United States Patent [19]

Klun et al.

[11] 4,451,667
[45] May 29, 1984

[54] PREPARATION OF ACRYLATE ESTERS FROM VINYL HALIDES AND ORGANIC CARBONATES

[75] Inventors: Robert T. Klun; Thomas W. Regulski, both of Midland, Mich.

[73] Assignee: The Dow Chemical Company, Midland, Mich.

[21] Appl. No.: 411,725

[22] Filed: Aug. 26, 1982

[51] Int. Cl.$^3$ .............................................. C07C 67/36
[52] U.S. Cl. ...................................... 560/207; 560/101; 560/104; 560/114; 560/130; 560/142; 560/206; 260/464; 260/465 D; 260/465.4
[58] Field of Search ............... 560/206, 207, 234, 101, 560/104, 114, 130, 142; 260/544 A, 464, 465 D, 465.4

[56] References Cited

U.S. PATENT DOCUMENTS

| | | | |
|---|---|---|---|
| 3,337,611 | 8/1967 | Bearden | 560/234 |
| 3,457,299 | 7/1969 | Closson et al. | 560/207 |
| 3,626,005 | 12/1971 | Scheben et al. | 560/207 |
| 3,976,635 | 8/1976 | Itoh | 560/234 |
| 3,988,358 | 10/1976 | Heck | 560/207 |
| 3,991,101 | 11/1976 | Knifton | 560/207 |

FOREIGN PATENT DOCUMENTS 47-25050  7/1972  Japan .

OTHER PUBLICATIONS

Boeckmann, August et al., *Chemical Abstracts*, 70 (1969), #28,665q.
Patai, Saul, *The Chemistry of Carboxylic Acids and Esters*, (1969), Interscience, pub. 1, pp. 388–390.

*Primary Examiner*—Natalie Trousof
*Assistant Examiner*—L. Hendriksen
*Attorney, Agent, or Firm*—Norman L. Sims

[57] ABSTRACT

This invention is a process for the preparation of acrylate esters comprising contacting a vinyl halide with carbon monoxide and an organic carbonate in the presence of an effective amount of a group VIII metal catalyst.

9 Claims, No Drawings

PREPARATION OF ACRYLATE ESTERS FROM VINYL HALIDES AND ORGANIC CARBONATES

BACKGROUND OF THE INVENTION

This invention relates to the preparation of acrylate esters. More specifically, acrylate esters are prepared by the carbonylation of vinyl halides in the presence of an esterifying agent of an organic carbonate.

It is well-known that a vinyl halide can be carbonylated to prepare an acrylate ester. Heck, U.S. Pat. No. 3,988,358, Oct. 26, 1976 (incorporated herein by reference), teaches that a vinyl halide may be contacted with carbon monoxide and an alcohol or (poly)glycol in the presence of a homogeneous group VIII metal catalyst. Heck further teaches that it is necessary to include an amine as a hydrogen halide acceptor.

Closson et al., U.S. Pat. No. 3,457,299, July 22, 1969 (incorporated herein by reference), teaches that acrylate esters can be prepared by contacting vinyl halides with carbon monoxide and an alcohol or (poly)glycol in the presence of a heterogeneous group VIII metal catalyst. It is further taught that an excess of the alcohol or (poly)glycol can be used to act as a halogen acceptor so as to prevent the presence of free halogen in the reaction or the formation of hydrogen halide.

Scheben et al., U.S. Pat. No. 3,626,005, Dec. 7, 1971 (incorporated herein by reference), also teach that vinyl halides may be carbonylated to form acrylate esters in the presence of carbon monoxide and an alcohol or (poly)glycol with a group VIII metal catalyst. Scheben et al. further teach that either a homogeneous or heterogeneous catalyst may be used and that an excess of the alcohol or (poly)glycol may be used as a halogen acceptor.

It has been discovered that an organic carbonate may be used as an esterifying agent in a carbonylation. It has been further discovered that use of an excess amount of an organic carbonate functions as a halogen acceptor.

SUMMARY OF THE INVENTION

This invention is a process for the preparation of acrylate esters comprising contacting a vinyl halide with carbon monoxide and an organic carbonate in the presence of an effective amount of a group VIII metal catalyst.

The acrylate esters produced by this process are useful as monomers in the preparation of polymers which have use in preparing latexes and molded or cast articles including sheets and panels for glazing or other uses.

DETAILED DESCRIPTION OF THE INVENTION

The vinyl halide can be represented by the following formula

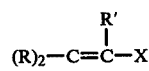   I wherein
X is a halogen;
R is separately in each occurrence hydrogen, alkyl, cycloalkyl or aryl; and
R' is hydrogen or methyl.
R is preferably hydrogen or alkyl, most preferably hydrogen. R' is preferably methyl.

The organic carbonates may be represented by the formula

   II wherein R" is separately in each occurrence aryl, alkyl, cycloalkyl or benzyl and may be substituted with an alkyl, aryl, cycloalkyl, nitro, cyano, ester, carboxylate, amide, aldehyde, hydroxyl, amino, substituted amino or halogen, if these groups are less reactive than the other groups in the reactants which are intended to take part in the reaction. R" is preferably a $C_{1-10}$ lower alkyl and most preferably methyl.

The acrylate ester prepared can be represented by the formula

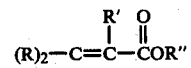   III wherein R, R' and R" are as defined above.

A halogen acceptor is used to reduce the presence of free halogen or hydrogen halide. The presence of a free halogen or hydrogen halide in the reaction can create problems because of its corrosive nature.

The halogen acceptor can be an excess of the organic carbonate compound used to esterify the vinyl halide. Alternatively, an amine can be used as the halogen acceptor. Suitable amines are tertiary amines. Inorganic compounds may also be used as halogen acceptors. Suitable inorganic halogen acceptors include calcium oxide, sodium carbonate, potassium hydroxide and the like. An excess of the organic carbonate is the preferred halogen acceptor.

Carbon monoxide is added to the reaction by pressurizing the reaction vessel or zone with carbon monoxide gas and maintaining positive pressure with carbon monoxide gas throughout the process. Carbon monoxide is thus present in an excess amount. Use of excess carbon monoxide increases yields. It is desirable to employ from about 1.0 to about 25 or more moles of carbon monoxide per each mole of vinyl halide. A preferred amount is from about 1.0 to about 15 moles.

The organic carbonate used to esterify the vinyl halide should be present in a molar ratio of the former to the latter of 1:1.

The catalyst is some form of a group VIII metal. Preferred group VIII metals are palladium, cobalt, rhodium, iridium, nickel or platinum, with palladium most preferred. The metals can be employed either as homogeneous or heterogeneous catalysts. Homogeneous catalysts are preferred when the reaction is run in the liquid phase.

When the group VIII metals are employed as heterogeneous catalysts, either the metal or a salt of the metal is supported on an inert carrier of activated carbon, silica alumina, silicalite, alumino silicates, activated clays, ion-exchange resins, or titanium, zirconium, magnesium, aluminum or silicon, or oxides thereof. Alumina supports are preferred.

Where palladium is used as the catalyst, between about 0.1 and 10 percent by weight of the support of palladium can be used, preferably between about 0.1 and 2.0 percent by weight of the support.

The reaction temperature is between about 150° C. and 300° C. for a heterogeneous catalyst, preferably between about 220° C. and 250° C. Pressure should be between about 100 and 5000 psi, preferably between about 400 and 1000 psi.

The group VIII metal can also be used as a homogeneous catalyst. In this form the metal is used in a complex in which the metal can be reduced to the zero valence state, as it is believed that the catalytic species of these metals are the zero valent species. The complex can be represented by the formula $Y_mB(LR_3''')_p$ wherein B is a group VIII metal; Y is chlorine, bromine, iodine, fluorine, acetate, $NO_3$ and the like; L is nitrogen, phosphorus or arsenic; m is an integer between 0 and 2; p is an integer between 0 and 4; and R''' is separately in each occurrence, alkyl, aryl, alkoxy, aryloxy, thioalkyl, thioaryl or acetate.

L is preferably phosphorus; R''' is preferably alkyl, aryl or acetate; and B is preferably palladium, cobalt, rhodium, iridium, nickel or platinum and most preferably palladium. Both m and p are preferably 2.

These complexes may be prepared in situ, or prior to being added to the reaction vessel or zone. When palladium is used, between about 0.01 and 10 mole percent can be used, between about 0.1 and 1.0 mole percent is preferred.

The temperature for this reaction with a homogeneous catalyst is between about 50° C. and 200° C., preferably 100° C. and 160° C. Below 50° C., the reaction rate is too low, at 160° C. the catalyst begins to decompose.

The process disclosed herein is usually run in a solvent. The solvent can be an excess of organic carbonate. Alternatively, this step may be carried out in the presence of an inert solvent such as a hydrocarbon or a (poly)glycol diether. The hydrocarbons employed can be either aliphatic, alicyclic or aromatic. Suitable solvents include cyclohexane, benzene, toluene, isooctane, xylene, mesitylene, ether, kerosene, No. 9 oil and (poly)alkylene glycol diethers. Of the above-described solvents, those with a boiling point above 160° C. are preferred for use with a homogeneous catalyst as such catalysts decompose above 160° C. Ethylene glycol dimethyl ether is a preferred solvent for use with the homogeneous catalyst.

In one embodiment the vinyl halide is 2-halo-1-alkene, the organic carbonate is dimethyl carbonate and the acrylate ester prepared is methyl methacrylate.

Organic halides, such as methyl bromide, are by-products of the reaction in the carbonylation and esterification where an organic carbonate is used as the halogen acceptor. The organic halide may itself be commercially valuable.

SPECIFIC EMBODIMENTS

Having generally described the invention, a more complete understanding can be obtained by reference to the following example, which is included for the purpose of illustration and is not intended to limit the scope of the claims.

Example—Preparation of Methyl Methacrylate from 2-Bromopropene and Dimethyl Carbonate To a stirred high pressure reactor was added 45.0 g of dimethyl carbonate, 0.05 g of dinitro-orthosec-butylphenol and 1.30 g of dichlorobis(triphenylphosphine)palladium. The reactor was pressurized to 300 psig with carbon monoxide and heated to 150° C. Then 12.1 g of 2-bromopropene was added to the reaction mixture. After 52 hours the reactor was cooled to room temperature. Analysis of the product mixture showed high conversion of starting materials with methyl methacrylate as the major product.

What is claimed is:

1. A process for the preparation of acrylate esters comprising contacting a vinyl halide with carbon monoxide and an organic carbonate in the presence of an effective amount of a group VIII metal catalyst.

2. The process of claim 1 wherein the vinyl halide is represented by the formula

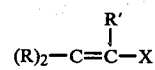

wherein

X is a halogen;

R is separately in each occurrence hydrogen, alkyl, cycloalkyl or aryl; and

R' is hydrogen or methyl.

3. The process of claim 1 wherein the organic carbonate is represented by the formula

wherein R'' is separately in each occurrence aryl, alkyl, cycloalkyl or benzyl and may be substituted with an alkyl, aryl, cycloalkyl, nitro, cyano, ester, carboxylate, amide, aldehyde, hydroxyl amino, substituted amino group or a halogen.

4. The process of claim 3 wherein R'' is a $C_{1-10}$ lower alkyl group.

5. The process of claim 3 wherein R'' is methyl.

6. The process of claim 2 wherein R is separately in each occurrence hydrogen or alkyl.

7. The process of claim 2 wherein R is hydrogen and R' is methyl.

8. The process of claim 1 wherein the vinyl halide is a 2-halopropene, the organic carbonate is dimethyl carbonate and the acrylate ester is methyl methacrylate.

9. The process of claim 1 wherein the molar ratio of organic carbonate to vinyl halide is 1:1 or greater.

* * * * *